United States Patent
Boβmeyer et al.

(10) Patent No.: US 8,835,176 B2
(45) Date of Patent: Sep. 16, 2014

(54) ANALYSIS OF MICROBES FROM MICROCOLONIES BY MALDI MASS SPECTROMETRY

(71) Applicant: Bruker Daltonik GmbH, Bremen (DE)

(72) Inventors: Jens Boβmeyer, Bremen (DE); Jochen Franzen, Bremen (DE)

(73) Assignee: Bruker Daltonik GmbH, Bremen (DE)

( * ) Notice: Subject to any disclaimer, the term of this patent is extended or adjusted under 35 U.S.C. 154(b) by 0 days.

(21) Appl. No.: 13/910,279

(22) Filed: Jun. 5, 2013

(65) Prior Publication Data

US 2013/0337502 A1 Dec. 19, 2013

(30) Foreign Application Priority Data

Jun. 8, 2012 (DE) .......................... 10 2012 011 648

(51) Int. Cl.
| | |
|---|---|
| G01N 30/72 | (2006.01) |
| C12N 1/06 | (2006.01) |
| H01J 49/04 | (2006.01) |
| G01N 27/62 | (2006.01) |
| C12Q 1/04 | (2006.01) |
| G01N 33/543 | (2006.01) |
| G01N 33/68 | (2006.01) |

(52) U.S. Cl.
CPC ............ *G01N 27/62* (2013.01); *H01J 49/0418* (2013.01); *C12Q 1/04* (2013.01); *G01N 33/5438* (2013.01); *G01N 33/6848* (2013.01)
USPC ...................................... 435/405; 435/173.7

(58) Field of Classification Search
None
See application file for complete search history.

(56) References Cited

U.S. PATENT DOCUMENTS 4,617,265 A * 10/1986 Peterson ....................... 435/7.37
5,808,300 A     9/1998 Caprioli 2007/0065946 A1   3/2007 Reboud et al.
2007/0275478 A1  11/2007 Taranenko et al.
2013/0337502 A1  12/2013 Boβmeyer et al.

FOREIGN PATENT DOCUMENTS

| DE | 102004020885 A1 | 11/2005 |
| DE | 60317314 T2 | 9/2008 |
| DE | 102009007266 A1 | 10/2010 |
| DE | 102010019869 A1 | 11/2011 |
| DE | 102010033105 A1 | 2/2012 |
| WO | 03044825 A1 | 5/2003 |
| WO | WO2013182648 A1 | 12/2013 |

OTHER PUBLICATIONS

Maquelin, K. et al. 2000. Raman spectroscopic method for identification of clinically relevant microorganisms growing on solid culture medium. Analytical Chemistry 72:12-19. specif. pp. 12-13, 16.*

* cited by examiner

Primary Examiner — John S Brusca
Assistant Examiner — Sharon M Papciak
(74) Attorney, Agent, or Firm — Robic, LLP

(57) ABSTRACT

The invention relates to the cell disruption of microbes and the preparation of the microbe proteins for mass spectrometric analysis. The cells of microbes from microcolonies are disrupted by physical or chemical means directly on the nutrient medium. The released proteins are then transferred to sample supports by direct contact with their contact surfaces; electrophoresis can be used for assistance. Once the proteins are firmly adsorbed on the contact surfaces, they can be washed with water in order to remove substances which interfere with the ionization process. For analysis by matrix-assisted laser desorption (MALDI), the proteins are prepared on the contact surfaces of the sample supports with matrix substances to form MALDI samples; the sample supports are then introduced into a MALDI mass spectrometer for the acquisition of mass spectra. The microbes are identified by similarity comparisons between the mass spectra of the microbe proteins and similarly obtained reference spectra.

19 Claims, 2 Drawing Sheets

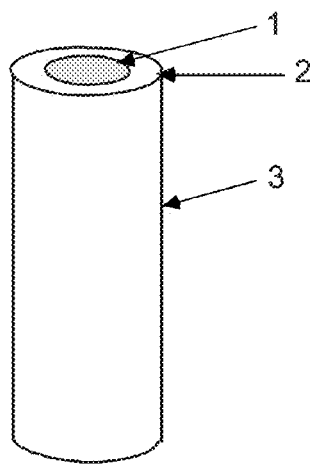
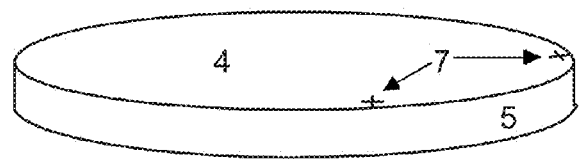
FIGURE 2
FIGURE 1
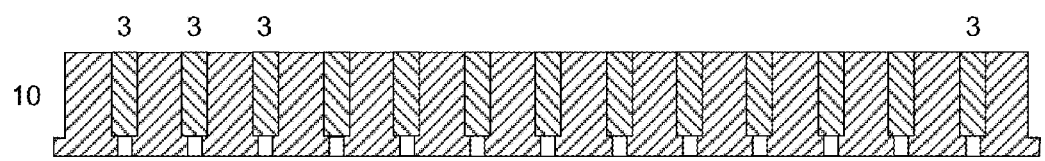
FIGURE 3
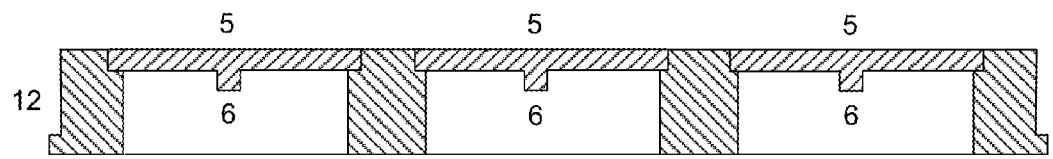
FIGURE 4

ANALYSIS OF MICROBES FROM MICROCOLONIES BY MALDI MASS SPECTROMETRY

BACKGROUND OF THE INVENTION

1. Field of the Invention

The invention relates to methods for the mass spectrometric analysis of microbes from colonies on surfaces of nutrient media, particularly in a mass spectrometer with ionization by matrix-assisted laser desorption (MALDI).

2. Description of the Related Art

The routine, fast and error-free analysis of microorganisms plays an important role particularly in clinical and extraclinical infection diagnostics, hygiene monitoring in hospitals or rivers and lakes used for swimming, food analysis, monitoring and control of biotechnological processes, and in microbiological research. The term microorganisms, here called microbes for short, describes all microscopically small organisms, for example unicellular fungi (e.g. yeasts), algae, or protozoae (e.g. plasmodia as malaria pathogens), although the focus of the identification work is usually on bacteria.

The identification of microbes means, in principle, determining their species and thus categorizing the microbes into the taxonomic hierarchy: domain (bacteria, archaea and eukaryotes), kingdom, phylum, class, order, family, genus, and species. In addition to taxonomic identification, the analysis of microbes can also comprise their characterization in terms of other properties, such as the pathogenicity of a microorganism (ability to cause disease), or the resistance of a microorganism against antibiotics.

For mass spectrometric identification methods, microbes taken from samples for analysis are usually cultured on nutrient media in Petri dishes to form colonies. The length of time between the samples for analysis being delivered to the analytical laboratory and the identification of the species is essentially dictated by the time needed for culturing, because the actual mass spectrometric determination takes only minutes. At present, this culturing process often takes between 18 and 24 hours. This is too long for many applications, particularly for applications in medical diagnostics. There is therefore an urgent need to significantly shorten the time required for the mass spectrometric identification, particularly to one working day.

With the methods currently used, the nutrient medium for the culture is usually contained in an agar in a Petri dish (agar plates), resulting in pure "isolates" in separated colonies. Agar is a gelatinous galactose polymer comprising much more than 90 percent water. The agar itself is indigestible and is attacked hardly at all by microbes. Since the microbes are mainly sampled manually at present, the colonies should have diameters of at least half a millimeter, better at least one millimeter, for reliable sampling of the microbes. To culture colonies of this size takes many hours, or sometimes even days, depending on the vigor of the microbes; for the clinically important species, the samples on agar plates are usually cultured for around 18 to 24 hours nowadays. If the colonies overlap or mix, isolated colonies are obtained in a second culture.

During the manual preparation of a MALDI sample, a small quantity of a selected colony is transferred from the surface of the nutrient medium onto a sample support; in practice this is often done with a wooden toothpick which is disposed of afterwards. The transferred microbes are then sprinkled with a strongly acidified solution of a conventional matrix substance (usually α-cyano-4-hydroxycinnamic acid, HCCA, or 2,5 dihydroxybenzoic acid, DHB) for a subsequent ionization by matrix-assisted laser desorption (MALDI). The acid (usually formic acid or trifluoroacetic acid) attacks the cell walls, which means that the organic solvent (usually acetonitrile) of the matrix solution can penetrate into the microbial cells and cause their weakened cell walls to burst by osmotic pressure. The destruction of the usually resilient cell walls is called "cell disruption;" cell disruption releases the soluble proteins from the cell. The sample is then dried by evaporating the solvent, causing the dissolved matrix material to crystallize. The released soluble proteins of the microbes, and also other substances of the cell to a small extent, are incorporated into the matrix crystals during the crystallization. This process produces a sample preparation on the sample support, which is called "MALDI sample" below.

The MALDI samples with the embedded analyte molecules are bombarded with focused UV-laser pulses of a few nanoseconds duration in a mass spectrometer, thus generating ions of the analyte molecules in the vaporization plasmas. These ions can then be separated from each other in the mass spectrometer according to the mass of the ions, and can be measured. Currently, simple time-of-flight mass spectrometers without a reflector are used for the mass spectrometric identification of microbes in order to achieve the highest sensitivity.

The mass spectrum is the intensity profile of the mass values of the analyte ions from the microbes. The ions here are predominantly protein ions, and the ions with the most useful information for identification have masses of approximately between 3,000 daltons and 15,000 daltons. In this method the protein ions are predominantly only singly charged (charge number $z=1$), which is why one can also simply talk about the mass m of the ions here, instead of always using the term "mass-to-charge ratio" m/z, as is actually necessary in mass spectrometry. The identification is carried out by similarity comparisons between the mass spectra acquired from the microbes and reference spectra from a reference library; see the document DE 10 2010 006 450 A1 (M. Kostrzewa), which also contains a detailed description of the mass spectrometric method. For medical applications, suitable reference libraries with reference mass spectra from several thousand microbe strains are now commercially available.

The mass spectrometric method for the identification is very robust; changes to the culture conditions or the preparation methods have hardly any effect on the identification results because practically only genetically defined proteins with genetically defined abundances are analyzed for each species. Around 60 to 85 percent of the proteins originate from the ribosomes, which comprise a fixed number of between 40 and 60 different protein molecules, the number depending on the species. Each bacterial cell contains several ten thousand identical ribosomes; cells of eukaryotes contain several hundred thousand. Thus the abundances of the measured proteins do not depend on the nutritional conditions or the maturity of the colony, as is the case with lipoproteins or fatty acids serving as energy stores, for example. The robustness of the method makes it possible to use microbes from very young, or mature or even ageing colonies for identification, and approximately the same identification results are achieved for these colonies.

To date the rule of thumb has been that around 105 microbes, at least, are required for preparing the MALDI sample on the sample plate in order to guarantee a reliable mass spectrometric identification of the microbes. This quantity is hardly discernible with the naked eye. Particularly suitable are quantities between 105 and 107 microbes. In the case of eukaryote cells with several hundred thousand ribosomes, usable mass spectra have been successfully obtained from individual cells. But for bacteria, whose hard cell walls require special cell disruption processes, it has so far only been possible in rare cases to produce mass spectra which are good enough for an identification from only 10³ bacteria or less.

The mass spectrometric method of identification has proven to be extremely successful. It is very fast once culturing has been completed, and the certainty of correct identification is far greater than with the microbiological identification methods currently in use, as has been demonstrated in various studies.

The pursuit of automation has led to devices which replace manual transfer with machine transfer using a small inoculating rod. The Fraunhofer Institute for Factory Operation and Automation (Magdeburg/Germany) has developed a robot called "MiRob", which can perform this task (cf.: O. Lange et al. (2008) "MIROB: automatic rapid identification of microorganisms in high through-put", Industrial Robot: An International Journal, Vol. 35 Iss: 4, pp. 311-315 or patent DE 10 2004 020 885 B2). The robot is manufactured as Mi Rob 300i by the company Mess-, Prüf- and Handling-Systeme GmbH, Reutlingen/Germany. patent DE 10 2004 020 885 B2, O. Lange et al.). As is the case with manual transfer, the microbes are transferred indirectly onto the mass spectrometric sample support by means of a tool, in this case an inoculating rod. Here too, the colonies should have a minimum diameter of 0.5 millimeters. The transfer tools used to date (toothpicks, inoculating rods) are designed to be used only once.

It would be desirable to have methods for the mass spectrometric analysis of microbes with which the time required from the delivery of samples to be investigated (sample for analysis) through to the identification is significantly shortened in comparison with current methods, preferably to one working day. The method should also be reliable and capable of automation, and should require little consumable material.

SUMMARY OF THE INVENTION

The present invention provides a method for the mass spectrometric analysis of microbes on the surface of a nutrient medium by mass spectra of their proteins acquired in a mass spectrometer, comprising the steps of: (a) disrupting the cells of microbes on the surface of a nutrient medium, thereby releasing microbe proteins; (b) transferring the microbe proteins released onto a contact surface of a sample support by direct contact; and (c) acquiring mass spectra of the microbial proteins on the sample support.

The present invention also provides a method for the mass spectrometric analysis of microbes on the surface of a nutrient medium in a mass spectrometer with ionization by matrix-assisted laser desorption, wherein: (a) microbes are cell disrupted on the surface of the nutrient medium; (b) the microbe proteins released by the cell disruption are transferred by direct contact onto a contact surface of a sample support; (c) the transferred microbe proteins are prepared as a MALDI sample on the contact surface of the sample support; and (d) the sample support with the MALDI sample is transferred to the mass spectrometer for analysis. Other types of ionization where the substances to be ionized are located on a sample support can also be used instead of MALDI ionization, such as cluster ionization in accordance with EP 1 200 984 B1, Desorption Electrospray Ionization (DESI) in accordance with WO 2005/094389 A2 or Matrix Assisted Laser Desorption Electrospray Ionization (MALDESI) in accordance with DE 10 2004 002 729 A1. Here, the preparation of a mass spectrometric sample can comprise in the disruption of the microbial cells and the transfer of microbe proteins onto the sample support.

After only six to eight hours of culturing microcolonies with diameters between 50 and 200 micrometers have grown. The cells of the microbes of the microcolonies are disrupted directly on the surface of the nutrient medium, e.g., an agar surface, either physically or chemically by destroying the cell walls. The released proteins are then transferred to contact surfaces on sample supports by direct contact; the transfer may be assisted by electrophoresis. The contact surfaces can be bare metal or coated with strongly protein-adsorptive substances such as nitrocellulose (guncotton, collodion cotton) or α-cyano-4-hydroxycinnamic acid (HCCA). Once the proteins are firmly adsorbed on the contact surfaces, they can be vigorously washed with water in order to remove salts, detergents and other substances which interfere with the MALDI process of ionization. The proteins are then prepared on the contact surfaces of the sample supports with matrix substances to form MALDI samples; the sample supports are then introduced into a MALDI mass spectrometer for the acquisition of the mass spectra, possibly after first being inserted into a suitable adapter plate. The microbes are identified by similarity comparisons between the measured mass spectra of these microbe proteins and reference mass spectra of a spectrum library.

The disrupted cells of the microbes can be brought into contact with the end of a pin-shaped sample support (sample support pin). The contact surface of the pin-shaped sample support is so small that only microbe proteins of one individual colony are transferred onto the pin-shaped sample support. After the microbe proteins have been transferred, the pin-shaped sample support is preferably inserted into an adapter plate in such a way that the end surface of the pin-shaped sample support is essentially flush with the surface of the adapter plate. Here, "essentially flush" means that a mass spectrometric analysis in a MALDI time-of-flight mass spectrometer with axial ion injection is possible with sufficient resolution. Microbes from different colonies can each be transferred onto one of several pin-shaped sample supports, which are inserted together into an adapter plate and introduced into the mass spectrometer in the adapter plate. It is also possible to transfer microbes from one colony onto several pin-shaped sample supports. The end surfaces of the pin-shaped sample supports preferably have surface areas of less than nine square millimeters, in particular of less than four square millimeters.

A method according to the invention using pin-shaped sample supports comprises the following steps, for example: taking an image of the surface of the nutrient medium, determining the positions of colonies from the image, disrupting the microbe cells at the determined positions, transferring the cell proteins of the disrupted microbes at the determined positions onto separate pin-shaped sample supports, inserting the pin-shaped sample supports into an adapter plate, preparing MALDI samples of the microbe proteins on the pin-shaped sample supports, introducing the adapter plate into a mass spectrometer acquiring mass spectra with ionization by matrix-assisted laser desorption at the positions of the pin-shaped sample supports in the adapter plate. The method may further comprise identifying the microbes by comparison of these mass spectra with reference mass spectra.

The disrupted microbe cells and thus their proteins can also be brought into contact with a plate-shaped sample support (sample support plate). The contact surface of the plate-shaped sample support is so large that microbe proteins from several colonies can be simultaneously transferred onto the plate-shaped sample support. The contact surface here is preferably aligned parallel to the surface of the nutrient medium and lowered, or lightly pressed, onto the surface. After the transfer, one or more plate-shaped sample supports can be arranged on an adapter plate and fastened there, by mechanical or magnetic forces, for example. The contact surface of a plate-shaped sample support can have a diameter of approximately between one and eight centimeters, for example, and in particular be adapted to the inside diameter of a Petri dish used for the culture.

When a plate-shaped sample support is used, the surface of the nutrient medium can be imaged before or after cell disruption of the microbes, and the position of the plate-shaped sample support relative to the surface of the nutrient medium can be determined during the contact transfer. From the image and the position it is possible to determine the positions of the transferred microbe proteins on the sample support. The MALDI samples are preferably prepared only at the determined positions, and the mass spectrometric analyses are carried out only on the prepared MALDI samples. It is also possible, however, to prepare a matrix layer on the whole contact surface of the sample support and to carry out the mass spectrometric analyses only at the determined positions. Furthermore, during application (inoculation) of the sample for analysis onto the surface of the nutrient medium, the track of the application (inoculation) can be recorded and the mass spectrometric analyses can be carried out only along the recorded track.

The invention thus provides methods for acquiring mass spectra of the microbe proteins that are suitable for the identification and require a culture period of only around eight hours at maximum for most of the clinically important microbes, which means that the mass spectrometric analytical method takes less than one working day. In this short period of time, only microcolonies with around 103 to 105 microbes form on agar. Even for slow-growing microbes, which until now have had to be cultured for many days, the time for an identification can be reduced to half, or even a quarter, of the time required to date.

The cell disruption of the microbes, i.e. the destruction of their cell walls, can be effected physically by ultrasound, electromagnetic radiation (e.g. infrared radiation) or high pressure (more precisely the sudden pressure release). It is possible for the positions of colonies on the surface of the nutrient medium to be determined, and colonies selected, and for the ultrasound or infrared radiation to have a localized effect on the selected colonies. For example, narrowly focused infrared radiation from laser diodes can cause the microbes to burst. With an ultrasound micro-tip at 20 to 30 kilohertz, a targeted cell disruption of all microbes of a microcolony can be performed in a very short time without damaging the proteins in the interior of the cell. Mechanical destruction is also possible: with the nitrogen decompression method, nitrogen is first dissolved in the microbes at high pressure; a rapid decompression then causes the microbes to burst.

The microbes can also be chemically cell disrupted by the addition of a substance, usually present in dissolved form. Chemical cell disruption can be achieved, for example, by the enzyme lysozyme (also called muramidase); the enzyme attacks the muramine lattice (the peptidoglycan envelope) of bacterial cell walls. For gram-negative bacteria a small quantity of ethylenediaminetetraacetic acid (EDTA) must first be added before the lysozyme can take effect. A final addition of Octoxinol 9 (Triton® X-100), a non-ionic tenside from the group of octylphenol ethoxylates, then lyses the cell wall. The cell wall can also be weakened by acids such as formic acid or trifluoroacetic acid in such a way that the addition of a solvent-water mixture can penetrate into the cells and cause them to burst by osmotic pressure. As is the case with a localized physical cell disruption, it is also possible here to determine the positions of colonies on the surface of the nutrient medium, to select colonies and to add the cell weakening or disrupting substance to the selected colonies in a localized way in each case. On the other hand, the cell disrupting substance can also be sprayed over the surface of the nutrient medium.

The contact surface of the sample supports can, for example, be the surface of a sample support plate of any shape, measuring around one to eight centimeters in diameter, which can simultaneously pick up the microbe proteins of many cell disrupted colonies by being gently pressed onto an agar surface. Or it can be simply the end surface of a thin sample support pin measuring only around two millimeters in diameter for the removal of microbe proteins from only one selected colony in each case.

The surface of the nutrient media is preferably imaged before the microbes are cell disrupted in order to obtain information on the position of the colonies, in particular the microcolonies. The positional data can serve to control the physical or chemical cell disruption and to control the transfer of the microbe proteins from the nutrient media onto the contact surface, in particular the transfer to thin sample support pins. The positional data from the digital image can, however, also be used to control the scanning of larger sample support plates with the laser beam during the acquisition of spectra. The surface of the nutrient medium is preferably imaged with the aid of light-optical measurement procedures, most preferably with a reflected-light microscope in the visible spectral range. The light-optical measurement procedure can also be a spatially resolved measurement of scattered light, Raman scattering or fluorescence. The surface of the nutrient medium is preferably imaged before the microbes are cell disrupted, but the imaging can also be done after a full-area cell disruption of the microbes.

The methods according to the invention have the advantage over the prior art that they require less consumable material because transfer tools are not required, and they are therefore lower cost and that they require less microbe material because of the direct transfer of proteins, and offer a high sensitivity because the proteins can be washed rigorously and so freed from all salts, tensides and other material which deteriorates the MALDI sensitivity. Compared to the manual transfer of microbes from different samples for analysis onto a mass spectrometric sample support, transfer via direct contact makes it possible to avoid mistakes in the sample assignation, by automatically transferring an identification label of each sample for analysis to each mass spectrometric sample support used. This identification label is stored on the support of the nutrient medium. This identification label can be combined by positional data and the identification label of the Petri dish. Transferring the microbe proteins with the aid of a protein-adsorptive coating allows MALDI mass spectra to be acquired with minimal signal suppression of the microbe proteins, particularly if the surface is additionally purified after the transfer of the microbe proteins.

BRIEF DESCRIPTION OF THE DRAWINGS

FIG. 1 depicts an example for a simple sample support pin (3), with an end surface acting as the contact surface, which is coated in the center (1) with a protein-adsorptive layer and has a border (2) which can be uncoated, but can also be coated with a hydrophobic layer, for example. The sample support pin (3) has a diameter of around 2 millimeters in this example, and is around eight millimeters long.

FIG. 2 shows a sample support plate (5) with contact surface (4) and positional markings (7) on the contact surface. The sample support plate (5) is round in this example, but can also be any other shape and any size between one and eight centimeters in diameter. The area of the sample support plate preferably corresponds to the area of the nutrient medium, i.e. approximately the shape and area of a Petri dish.

FIG. 3 shows how the sample support pins (3) are inserted into an adapter plate (10) in such a way that their end surfaces are flush with the surface of the adapter plate.

FIG. 4 shows an adapter plate (12) with sample support plates (5) which are inserted so as to be flush. The sample support plates (5) have handles (6) on the rear with which they can be gripped by a robotic system and pressed onto the plates of nutrient medium.

DETAILED DESCRIPTION

For the embodiments described below, a sample for analysis with unknown microbes, usually bacteria, is plated (inoculated) in the usual way onto agar in a Petri dish, and cultured in an incubator for six to eight hours at optimum temperature (usually 37° Celsius). Most of the clinically relevant, pathogenic microbes divide after periods of between 15 and 45 minutes (this is called the "generation time"). In six hours, virulent microbes experience 24 generations, slower ones with 45 minutes generation time only about eight generations. After ten generations, the microcolonies should theoretically contain around $10^3$ microbes; after twenty generations, around $10^6$ microbes. The colonies grow on the surface of the nutrient medium; at higher numbers of generations, however, the growth on the agar is so strongly restricted that the theoretical values are not achieved. There are also clinically important exceptions with slow growth which require special treatment.

Figure 5:
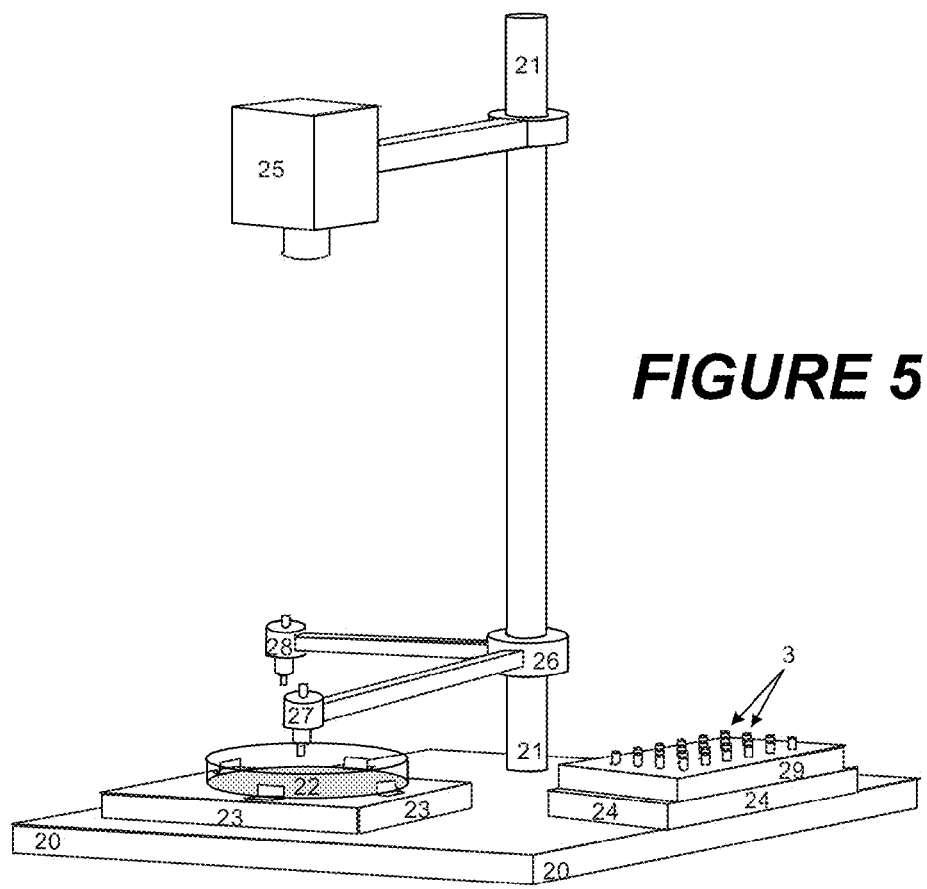
FIG. 5 shows a device for the cell disruption of the microbes of a colony in a Petri dish (22) and for the transfer of the microbe proteins onto sample support pins (3). The device has a base (20) on which two movement units (23) and (24) are located each acting horizontally in two directions, for the accurate positioning of the Petri dish (22) and a storage container (29) for sample support pins. A camera (25) and a joint (26) with two rigid arms are mounted on the support column (21). Attached to the arms are holders (27) and (28) for tools, with which ultrasonic tips, microdispensers or sample support pins, depending on the method used, can be moved vertically in order to lower them onto the agar, for example. Sample support pins can be taken from the storage container (29) and put back again. The joint (26) can be rotated between fixed angular positions in order to position the different tools above the agar. Fine adjustment of the position is done by the movement unit (23), controlled by positional data from the image of the camera (25).

The cell disruption on the nutrient surface can preferably be carried in a device as depicted in FIG. 5. The Petri dish (22) is fastened on the movement device (23) with clamps. Before the microbes are cell disrupted, it is expedient to take greatly enlarged images of the surface of the nutrient medium in the Petri dish (22) with a high-resolution digital camera (25) (or a reflected-light microscope) in order to determine the positions of microcolonies. Microcolonies with only 1000 bacteria have an approximate diameter of 0.05 millimeters; these can be photographically identified if the lighting is correct and they are enlarged. The positional data of the microcolonies can be determined automatically with the aid of image recognition methods; it is then possible to also automate the selection of the microcolonies for identification by specifying parameters for a characterization of the microcolonies. The parameters can particularly relate to the size, shape, reflection intensity and color of the microcolonies. It is also possible to determine the microcolonies visually by clicking on their position on a screen displaying the image, and thus select them for cell disruption and transfer of the released proteins.

We first describe a method which operates with cell disruption of the microbes of selected microcolonies by ultrasound. The device used here is an ultrasonic device at 20 to 30 kilohertz, which is equipped with a booster horn between 12.5 and 8 centimeters in length, made of titanium, with a micro-tip whose end surface has a diameter of around only one millimeter. The length must be exactly $\lambda/2$ in order to oscillate in resonance and to provide a high oscillation amplitude of up to one micrometer. The micro-tip is fastened to the holder (28), for example, which can swivel over the Petri dish (22) by rotating the joint (26). The microcolony is moved by the movement device (23) until it is precisely underneath the micro-tip; the movement device (23) for the Petri dish is controlled using the positional data from the images of the camera (25). The tip is moistened with water and lowered onto the colony. After lowering the ultrasonic tip onto the colony, the cell walls of the microbes are destroyed within a few seconds by the generation of cavitations; the soluble proteins are released.

Immediately after cell disruption, a pin-shaped sample support (3) is lowered onto the colony by the holder (27) in order to bind the free proteins to the contact surface. This is preferably done using the same device as shown in FIG. 5, which also lowered the ultrasonic micro-tip onto the colony. The transfer uses small sample support pins (3), as depicted in FIG. 1. The device according to FIG. 5 allows sample support pins (3) to be removed from a positionable storage container (29) and returned again. The end surfaces of the sample support pins (3) are each lowered centrally onto a cell disrupted microcolony or, when a liquid drop is present, are brought into contact with it in order to transfer the proteins from the microcolonies by contact onto the end surfaces of the sample support pins (3). A sample support pin (3) measuring two millimeters in diameter is shown in FIG. 1; the end surface should measure not more than around nine, preferably less than four, square millimeters. The sample support pins (3) must consist of electrically conductive material, such as metal or conductive plastic. They can later be inserted into appropriate closely fitting insertion holes of suitable adapter plates (10) which are suitable for being introduced into the MALDI mass spectrometer. The end surfaces of the sample support pins (3) can be bare, roughened or smooth; but they can also be prepared in a special way with protein-adsorptive layers (1), as shown in FIG. 1, with a border (2) which is either uncoated or carries a hydrophobic layer. The sample support pins (3) are usually designed for single use, as is advantageous for diagnostic methods. The preparation for the MALDI process and the laser desorption itself also take place on this end surface.

Thin coatings of nitrocellulose, as are used as blot membranes in gel electrophoresis, can serve as protein-adsorptive layers, for example. For this purpose a small quantity of guncotton (predominantly cellulose trinitrate) or collodion cotton (predominantly cellulose dinitrate) dissolved in a large quantity of acetone can be applied like a thin lacquer and dried. The nitrocellulose layer should be very thin; one micrometer thick at most. These nitrocellulose layers bind the proteins extremely tightly by adsorption, so the layers can be thoroughly washed with water after being coated with proteins. The sample support pins with the nitrocellulose layers are moistened and placed on the microbe colony with their cells disrupted. Repeated dabbing, or a to-and-fro movement, helps to bind the proteins more quickly on the contact surface.

In a special embodiment, the protein transfer can be assisted by electrophoresis. For this, the microbe colony must be sprinkled with a solution of SDS (sodium dodecyl sulfate) before or after the cell disruption. The molecules of SDS attach to the released proteins and form an excess negative charge. If an electrode is placed under the agar in the Petri dish (22), a positive voltage applied to the sample support pin (3) can quantitatively extract the free proteins from the agar and bond them to the nitrocellulose layer. The SDS can then be completely washed off the end surface of the sample support pin (3) without proteins being lost in the process. This method is particularly suitable if the agar liquefies due to the ultrasonic probe being lowered onto it, but quickly gels again after the sonication has finished, and embeds the released proteins.

During the subsequent preparation of the proteins on the nitrocellulose layers to create MALDI samples, the solvent for the matrix substance should also contain acetone or acetonitrile in order to dissolve the thin nitrocellulose layer and release the proteins again. During the vaporization of the solvent and the crystallization of the matrix substance, the protein molecules are incorporated into the matrix crystals as usual.

The nitrocellulose remaining in the MALDI sample does not interfere with the MALDI process of ionization, because it has the same effect as a matrix substance. The suggestion has already been made that nitrocellulose be used alone or in mixtures with other matrix substances for the ionization by matrix-assisted laser desorption; see document DE 196 17 011 C2 (C. Köster and J. Franzen, 1996). There have been no investigations as yet into whether the thin layer of nitrocellulose with the adsorbed protein molecules can be used alone and independently as a MALDI sample. It is, however, possible to produce a lacquer-like layer from a mixture of nitrocellulose with HCCA. This layer can then be used both for the adsorption and for the ionization.

Another version of a protein-adsorptive layer consists of matrix material, for example water-insoluble HCCA (α-cyano-4-hydroxycinnamic acid). A thin HCCA layer also adsorbs proteins so tightly that salts, detergents and other interfering substances can be carefully washed off. After drying, the thin HCCA layer can be dissolved slightly with a small quantity of acetonitrile. As the acetonitrile evaporates, the thin layer recrystallizes and embeds the protein molecules into the thin layer.

We now consider a method for disrupting the cell by chemical means. Chemical cell digestion with Lysozyme (a muramidase) enzymatically attacks the muramine lattice of the peptidoglycan envelope of the bacterial cell walls. There are several types of lysozyme with similar structure and the same effect. Since gram-negative bacteria have an outer cell membrane with lipopolysaccharides, which cannot be permeated by the lysozymes, a small quantity of ethylenediaminetetraacetic acid (EDTA) must first be used. This dissolves the lipopolysaccharides so that the lysozyme can act. A final addition of Octoxinol 9 (Triton® X-100), a non-ionic tenside from the group of octylphenol ethoxylates, then lyses the cell wall and simultaneously prevents the aggregation of the proteins.

The different solutions of EDTA, lysozyme or Octoxinol 9 can be applied, either individually or mixed, to individual microcolonies using microdispensers (for example piezo-microdispensers). The microdispenser can be mounted on the holder (28) of the device from FIG. 5, for example. If the microbes of a colony are cell disrupted, the released proteins can be transferred to the end surface of a sample support pin, as was described above. EDTA and Octoxinol 9 can be easily washed off. The lysozyme (around 14.3 kilodaltons) can appear in the mass spectrum; this must be taken into account in the identification by similarity comparisons with reference spectra.

The cell wall can also be weakened by means of acids such as formic acid or trifluoroacetic acid in such a way that the addition of a solvent-water mixture can penetrate into the cells and cause them to burst by osmotic pressure.

The use of sample support pins to transfer the proteins from a few selected colonies has the advantage that the Petri dish with the nutrient medium can be cultured further in order to later identify slow-growing microbes also.

Favorably the preparation of the transferred proteins on the end surfaces of the sample support pins (3) takes place when the sample support pins (3) have been inserted into the adapter plate (10); the preparation can then be done in pipetting robots. With thin HCCA layers, the released proteins can be prepared with the matrix substance simply by means of a drop (around 0.5 microliters) of acetonitrile, which slightly dissolves the thin layer and causes recrystallization as it evaporates. The proteins are embedded into the HCCA thin layers in this process. With nitrocellulose layers, the solution of the matrix substance must now be added. A non-contact deposition process has proven to be successful for depositing the small quantities of liquid; a small drop is pressed out of a central cannula in a controlled way, and a short pressure surge of a gas from a second, concentric cannula releases the drop and lets it fall onto the target.

The preparation of 96 samples can be carried out in less than ten minutes. The adapter plate (10) with the fully prepared MALDI samples can then be introduced into the ion source of a mass spectrometer via a vacuum lock. The acquisition of mass spectra, each composed of hundreds of individual spectra, requires only around one second per sample in modern MALDI mass spectrometers. If the identification program can operate quickly enough, the identification results for 96 MALDI samples can be available less than five minutes after the introduction of the adapter plates. The total time required for the work after completion of the culture, i.e. cell disruption, contact transfer, sample preparation, spectrum acquisition and identification, thus amounts to around half an hour.

A further embodiment of the transfer method concerns simultaneous contact transfer of the proteins from many colonies or microcolonies onto the contact surface (4) of a larger sample support plate (5). For individual colonies, the cell disruption here can be carried out chemically or with ultrasound on an individual basis, as described above. But it can also be done simultaneously for all colonies on the agar. The simultaneous cell disruption is best carried out chemically with aerosols of the required solutions, where the droplets of the aerosols are deposited on the agar in order to obtain a uniform preparation without strong lateral smearing of the proteins. Large-area preparation methods of this type and appropriate devices are shown in the document DE 10 2006 059 695 B3 (M. Schürenberg, identical to GB 2 446 251 A and US 2008/0142703 A1).

A sample support plate (5) with a round design is shown as an example in FIG. 2. In principle, the sample support plate (5) can be any shape with a diameter between one and eight centimeters. By being lowered, or lightly pressed, onto the surface of the nutrient medium, it can simultaneously pick up the proteins of several cell disrupted microcolonies. The sample support plate (5) can be pressed on manually or, for example, by means of a device which allows the contact pressure and the parallel alignment to be controlled. The surface (4) of this sample support plate (5) can be prepared in a similar way to the sample support pins in order to bind the proteins as effectively as possible. It can be coated with the same strongly adsorptive layers as the sample support pins, for example. Here too, electrophoresis may be used for transferring the proteins. The sample support plates (5) have markings (7) on their front and rear, which serve to determine their position and orientation. It is expedient if a camera takes a digital image of the rear of the sample support plate after it has been lowered onto the surface in order to document the positions relative to the colonies on the agar. The positions of the transferred microcolonies on the front of the plate can be determined from this image.

The sample support plates (5) can also be inserted into specially shaped adapter plates (12). The adapter plates (12) have an outer contour which is necessary for introducing them into the ion source of the mass spectrometer. From the positions of the markings visible on the front of the sample support plates, the positions of the microbe proteins from the colonies relative to the adapter plate can be determined. With knowledge of these positions, the laser beam can be controlled for the spectrum acquisition in such a way that only those positions are scanned which contain proteins from the cell disrupted microcolonies. Spectrum acquisition from the sample support plates can, in principle, also consist in scanning the whole contact surface, although this is usually too time-consuming. It is therefore better to use the positional data from the digital images and include only the identified positions of the microcolonies and their immediate surroundings in the spectrum acquisition.

Figure 6:
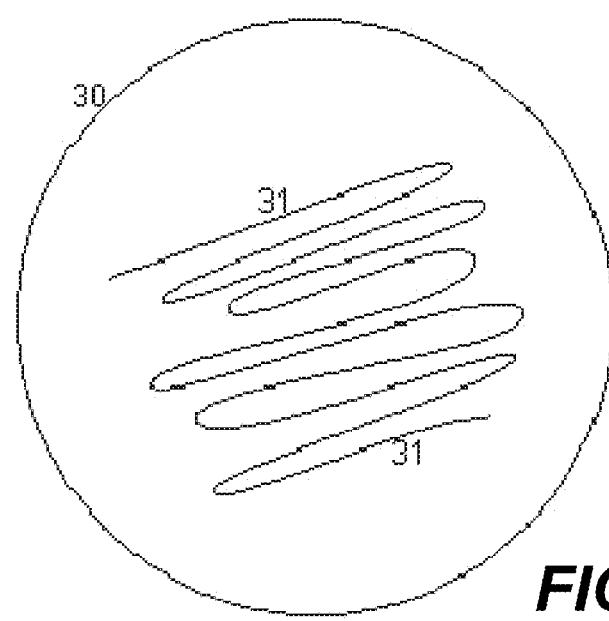
FIG. 6 depicts a Petri dish (30) in plan view, with a track (31) of a manually applied analyte solution. The application process can be digitally photographed, and after the microbes have been cultured, the image (or video recording) can serve to specifically digest the microbes along the track and to control the laser scanning on the contact surface of the sample support plate during the mass spectrometric analysis.

A special embodiment of the spectrum acquisition on larger sample support plates can consist in acquiring the mass spectra only along the track (31) of the samples for analysis that have been plated (inoculated) onto the surface of the nutrient medium in a Petri dish (30) (FIG. 6). To this end it is necessary to photographically record the plating (inoculation track) of the sample for analysis onto the agar plate, with the aid of a long exposure or a video camera, for example. The cell disruption is best undertaken chemically on the whole surface of the nutrient medium. Following the track without previously imaging the surface of the nutrient medium makes it possible to also identify microbes in microcolonies which are not yet discernible in a corresponding image, without having to mass spectrometrically analyze the whole sample support. It is, furthermore, possible to prepare the MALDI samples only along the track determined. It has to be considered, however, that the colonies sometimes do not grow directly on the track because some microbes first move on the surface for a while before they found a colony.

The described methods of cell disruption, transfer and preparation can be modified or extended in a variety of ways. In particular, it is possible to continue to culture the remaining microbes of the undestroyed microbe colonies in the Petri dishes after the microbe proteins have been removed with the aid of sample support pins or sample support plates in order to also discover and identify more slowly growing microbes, albeit after a longer culture period. It may be expedient here to destroy the fast-growing microbes in undestroyed colonies or to remove them mechanically. The digital images which were taken after the short culture period are also helpful here in order to discover further colonies after longer culturing. These can be cell disrupted, removed with sample support pins or sample support plates and analyzed for identification, just like the original microcolonies.

If it is suspected that particularly slow-growing but dangerous microbes are present, a special embodiment of the method allows the Petri dishes with the nutrient media to be repeatedly examined at suitable intervals, every eight hours, for example, for the growth of microcolonies. If fast-growing microbes which are not of interest here are present and cause interference, the microcolonies of these microbes can be destroyed in these analytical cycles, or be removed completely. This reduces the danger that the fast-growing microbes will overgrow the slow-growing ones. The slow-growing microbes can be identified using specified features, such as their slow growth, but also other features such as the shape and color of the colonies. They are then cell disrupted on the agar; their proteins are removed from the surface of the nutrient medium by contact transfer onto sample support pins and, after preparation as MALDI samples, they are forwarded to the analysis in a MALDI mass spectrometer.

What is claimed is:

1. A method for the mass spectrometric analysis of microbes on the surface of a nutrient medium in a mass spectrometer with ionization by matrix-assisted laser desorption, comprising the steps:
    (a) disrupting the cells of microbes on the surface of the nutrient medium,
    (b) transferring the microbe proteins released by the cell disruption onto a contact surface of a sample support by direct contact of the contact surface with the cell disrupted microbes,
    (c) preparing the transferred microbe proteins as a MALDI sample on the contact surface of the sample support, and
    (d) transferring the sample support with the MALDI sample to the mass spectrometer.

2. A method according to claim 1, wherein the end surface of a pin-shaped sample support is brought into contact with the cell disrupted microbes, the contact surface of the pin-shaped sample support being so small that only microbe proteins of an individual colony are transferred onto the pin-shaped sample support.

3. A method according to claim 2, wherein, after the microbe proteins have been transferred, the pin-shaped sample support is inserted into an adapter plate in such a way that the end surface of the pin-shaped sample support is essentially flush with the surface of the adapter plate with a positive fit.

4. A method according to claim 3, with the steps:
    taking an image of the surface of the nutrient medium,
    determining the positions of colonies from the image,
    disrupting the microbes at the determined positions,
    transferring the cell disrupted microbe proteins at the determined positions onto a separate pin-shaped sample support,
    inserting the pin-shaped sample supports into an adapter plate,
    preparing MALDI samples from the microbe proteins on the pin-shaped sample supports,
    introducing the adapter plate into a mass spectrometer, and
    acquiring spectra with ionization by matrix-assisted laser desorption at the positions of the pin-shaped sample supports in the adapter plate.

5. A method according to one of the claim 4, wherein the end surfaces of the pin-shaped sample supports have surfaces of less than nine square millimeters, preferably less than four square millimeters.

6. A method according to claim 1, wherein a plate-shaped sample support is brought into contact with the cell disrupted microbes, and the contact surface of the plate-shaped sample support is so large that microbe proteins from microbes of several colonies are transferred simultaneously onto the plate-shaped sample support.

7. A method according to claim 6, wherein the surface of the nutrient medium is imaged before or after cell disruption of the microbes, the position of the plate-shaped sample support relative to the surface of the nutrient medium during the contact transfer is determined, and the positions of the microbe proteins on the sample support are determined from the image and the position of the sample support plate.

8. A method according to claim 7, wherein the MALDI samples are prepared only at the determined positions, and the mass spectrometric analyses are carried out only on the prepared MALDI samples, or a matrix layer is prepared on the whole of the contact surface of the sample support and the mass spectrometric analyses are carried out only at the determined positions.

9. A method according to claim 6, wherein, during inoculation of the sample for analysis onto the surface of the nutrient medium, the track of the inoculation is recorded and the mass spectrometric analyses are carried out only along the recorded track.

10. A method according to claim 1, wherein the microbes are cultured on the surface of the nutrient medium for less than eight hours before being cell disrupted.

11. A method according to claim 1, wherein the cells of the microbes are disrupted physically on the surface of the nutrient medium by ultrasound, infrared radiation or high pressure.

12. A method according to claim 11, wherein the positions of colonies on the surface of the nutrient medium are determined, colonies are selected, and the ultrasound or the infrared radiation has a localized effect on the colonies selected.

13. A method according to claim 1, wherein the cells of the microbes are disrupted chemically by adding substance solutions.

14. A method according to claim 13, wherein the positions of colonies on the surface of the nutrient medium are determined, colonies are selected, and the cell disrupting substance is added in a localized way to each of the selected colonies.

15. A method according to claim 13, wherein the substance is an acid or the enzyme lysozyme.

16. A method according to claim 1, wherein the contact surface of the sample support has a protein-adsorptive coating.

17. A method according to claim 16, wherein the protein-adsorptive coating consists of nitrocellulose or α-cyano-4-hydroxycinnamic acid (HCCA).

18. A method according to claim 17, wherein the microbe proteins are drawn onto the protein-adsorptive coatings by electrophoresis.

19. A method for the mass spectrometric analysis of microbes on the surface of a nutrient medium by mass spectra of their proteins acquired in a mass spectrometer, comprising the steps:

(a) disrupting the cells of microbes on the surface of a nutrient medium, thereby releasing microbe proteins, (b) transferring the microbe proteins released onto a contact surface of a sample support by direct contact, and (c) acquiring mass spectra of the microbial proteins on the sample support.

* * * * *